United States Patent [19]

Tonne et al.

[11] Patent Number: 4,464,537

[45] Date of Patent: Aug. 7, 1984

[54] PREPARATION OF SACCHARIN

[75] Inventors: Peter Tonne, Neustadt; Hagen Jaedicke, Ludwigshafen, both of Fed. Rep. of Germany

[73] Assignee: BASF Aktiengesellschaft, Ludwigshafen, Fed. Rep. of Germany

[21] Appl. No.: 320,333

[22] Filed: Nov. 12, 1981

[30] Foreign Application Priority Data

Nov. 24, 1980 [DE] Fed. Rep. of Germany ....... 3044112

[51] Int. Cl.$^3$ .......................................... C07D 275/06
[52] U.S. Cl. .................................................. 548/211
[58] Field of Search ......................................... 548/211

[56] References Cited

U.S. PATENT DOCUMENTS

| | | | |
|---|---|---|---|
| 2,667,503 | 7/1951 | Senn | 548/211 |
| 3,759,936 | 9/1973 | Mounier | 548/211 |
| 4,042,600 | 8/1977 | DiPippo | 548/211 |
| 4,076,721 | 2/1978 | Koike et al. | 548/211 |
| 4,145,349 | 3/1979 | Bebbington | 548/211 |
| 4,259,499 | 3/1981 | DiPippo | 548/211 |

FOREIGN PATENT DOCUMENTS

| | | | |
|---|---|---|---|
| 301942 | 7/1900 | France | 548/211 |
| 7603836 | 12/1975 | Netherlands | 548/211 |
| 12585 | of 1900 | United Kingdom | 548/211 |

OTHER PUBLICATIONS

Barton, et al., *Comprehensive Organic Chemistry*, vol. 3, pp. 333 and 339 (1979).

Swann and Klias, "Investigation on Synthesis of Saccharine", Chemicals Committee, German Occupation, 1946.

Meerwin, et al., ". . . Aronatischer Sulfonsäwre–Chloride, . . . ", Chem. Ber., vol. 90, p. 841 (1957).

Barton and Ollis, *Comprehensive Organic Chemistry*, vol. 61, Pergamon, New York, (1979), pp. 950–958.

*Primary Examiner*—Donald G. Daus
*Assistant Examiner*—G. Hendricks
*Attorney, Agent, or Firm*—John H. Shurtleff

[57] ABSTRACT

A process for the preparation of saccharin by reacting an aqueous hydrochloric acid solution of o-methoxycarbonylbenzenediazonium chloride with sulfur dioxide, wherein (a) the aqueous diazonium salt solution is reacted with sulfur dioxide at from 0° to 100° C. in the presence of a water-immiscible or only partially water-miscible inert organic solvent, (b) in order to decompose the diazonium salt, the reaction mixture is treated simultaneously or subsequently with a diazonium salt decomposition catalyst, (c) the aqueous organic reaction mixture, or the organic phase obtained after removing the aqueous phase, is treated with an oxidizing agent at from 0° to 100° C. and (d) the organic phase is reacted with aqueous ammonia at from 0° to 50° C. and the saccharin is isolated from the aqueous phase in a conventional manner by acidifying with a strong acid.

11 Claims, No Drawings

PREPARATION OF SACCHARIN

The present invention relates to a novel process for the preparation of saccharin (I)

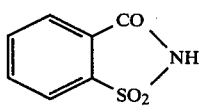

The preparation of this important compound, which is mainly used as a sweetener, is an extensively investigated problem, and correspondingly numerous processes and process improvements have been disclosed (compare, for example, Ullmanns Enzyklopädie der technischen Chemie, 3rd edition, volume 16, 1965, page 478 et seq.). Nevertheless, the classical method of synthesis, via sulfochlorination of toluene (Ullmann, loc. cit., page 479) has hitherto not been superseded in industrial operation, even though it is technically involved, requires expensive reagents and moreover gives relatively unsatisfactory yields (about 26%, based on toluene).

According to the method proposed in U.S. Pat. No. 4,042,600, I is prepared by diazotizing an anthranilic acid ester (II), reacting the aqueous solution of the diazonium salt (III) with sulfur dioxide in the presence of copper-I chloride and acetic acid to give the corresponding benzoic acid ester o-sulfochloride (IV), pyrolyzing IV to give the o-sulfobenzoic acid anhydride (V) and reacting V with ammonia, as illustrated by the following reaction scheme:

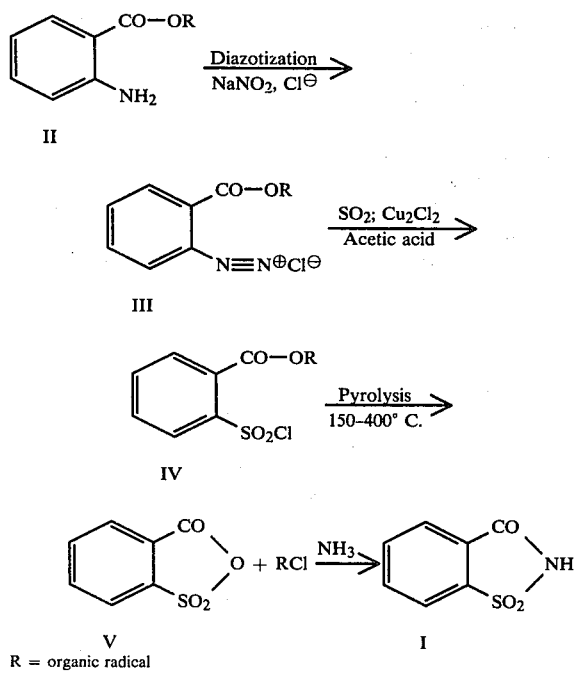

R = organic radical

However, this method is also involved because, inter alia, it requires isolation of the intermediates IV and V and because the pyrolysis, which in industrial operation is in any case difficult to control, is incomplete. Furthermore, the acetic acid cannot be recovered at economically justifiable expense.

The conversion of aryldiazonium chlorides to the corresponding sulfochlorides, similarly to step III→IV, has already been described by Meerwein et al. (Chem. Ber., 90 (1957), 841 et seq.), the addition of a water-insoluble solvent having a low dielectric constant, such as carbon tetrachloride and benzene, being recommended in order to improve the yield. Nevertheless, the yields obtained by this method, as illustrated by the examples of p-methoxybenzene-sulfochloride and β-naphthalene-sulfochloride, are unsatisfactory, being in each case about 40%.

Further, East German Pat. No. 4,564 discloses a synthesis of saccharin which also involves diazotizing an anthranilic acid ester and reacting the diazonium salt with $SO_2$. This process is however evidently unsatisfactory, both economically and technically, because, in order to avoid handling substantial volumes of water, the diazotization must be carried out with nitrous fumes and the further conversion must be carried out with liquid $SO_2$.

It is an object of the present invention to provide a simpler and more economical method of preparation of saccharin, in view of the unsatisfactory syntheses hitherto disclosed.

We have found that this object is achieved, and saccharin is obtained, by reacting an aqueous hydrochloric acid solution of o-methoxycarbonyl-benzenediazonium chloride with sulfur dioxide in an unusual reaction sequence, wherein (a) the diazonium salt solution is reacted with sulfur dioxide at from 0° to 100° C. in the presence of a water-immiscible or only partially water-miscible inert organic solvent, (b) in order to decompose the diazonium salt, the reaction mixture is treated simultaneously or subsequently with a diazonium salt decomposition catalyst, (c) the aqueous organic reaction mixture, or the organic phase obtained after removing the aqueous phase, is treated with an oxidizing agent at from 0° to 100° C. and (d) the organic phase is reacted with aqueous ammonia at from 0° to 50° C. and the saccharin is isolated from the aqueous phase in a conventional manner by acidifying with a strong acid.

The diazotization of methyl anthranilate, required before carrying out step (a), is known per se and therefore does not require detailed discussion. However, in order to achieve virtually complete diazotization and ensure the success of the process according to the invention it has proved particularly advantageous to effect the diazotization with sodium nitrite at from $-10°$ to $+10°$ C. in a hydrochloric acid medium, using from 1.5 to 4 moles of HCl and from 0.2 to 1 kg of water per mole of the anthranilic acid ester.

In step (a), the aqueous acidic solution, preferably containing from 10 to 40% by weight of the diazonium salt, is reacted with sulfur dioxide in the presence of a water-immiscible or only partially water-miscible inert organic solvent.

To achieve optimum yields of the reaction product, it is advantageous to employ not less than equimolar amounts of $SO_2$, based on the diazonium salt, but in general it is advisable to use the $SO_2$ in an excess of up to 1 mole, preferably of about 0.1 to 0.3 mole. The amount of the solvent is preferably from 0.1 to 1 liter per liter of aqueous diazonium salt solution, depending on the solubility of $SO_2$, and of the sulfochloride formed, in the solvent.

The solvent can in principle be any solvent which has insignificant miscibility with water, is substantially inert to aqueous acids and $SO_2$ and adequately dissolves $SO_2$ and the sulfochloride formed.

Good solubility of the sulfochloride is of particular importance, so that the choice of the solvent is especially guided by this consideration. In contrast, as regards sparing solubility in water, it suffices, in principle, that a separate organic phase forms. For technical reasons it is however advantageous to use a solvent which is highly water-insoluble, because this facilitates the separation—required by the need for recirculation—of the solvent from the aqueous phase.

Examples of suitable solvents are aliphatic ethers of 4 to 20 carbon atoms, eg. diethyl ether, di-n-propyl ether, diisopropyl ether, methyl ethyl ether and methyl tert.-butyl ether, aliphatic alcohols of 4 to 8 carbon atoms, eg. n-butanol, n-pentanol and the hexanols, aliphatic esters of 2 to 10 carbon atoms, eg. methyl acetate, ethyl acetate, n-propyl acetate, isopropyl acetate and the butyl acetates, aliphatic ketones of 4 to 10 carbon atoms, eg. methyl ethyl ketone, diethyl ketone, methyl isopropyl ketone and diisopropyl ketone, aliphatic chlorohydrocarbons of 1 to 4 carbon atoms, eg. methylene chloride and the dichloroethanes, dichloropropanes, trichloroethanes and trichloropropanes, chlorohydrocarbons having up to two chlorine atoms per carbon atom being generally preferred, aromatic hydrocarbons of 6 to 10 carbon atoms, eg. benzene, toluene and the xylenes, aromatic chlorohydrocarbons, eg. chlorobenzene, the dichlorobenzenes and the trichlorobenzenes, nitriles, eg. benzonitrile, nitro compounds, eg. nitrobenzene, and mixtures of these solvents.

For economic and technical reasons, solvents which boil at from 50° to 150° C. under atmospheric pressure are generally preferred, since these consume least energy in the distillation steps needed as part of the process in industrial operation. Amongst the groups of solvents mentioned, the ketones and aliphatic chlorohydrocarbons are particularly advantageous, whilst the aromatic solvents have proved somewhat less suitable.

The reaction can be carried out by thoroughly mixing a solution of the solvent and sulfur dioxide with the aqueous diazonium salt solution, or thoroughly mixing the three components, namely $SO_2$, solvent and aqueous phase. In both cases, it is advantageous to work at from 10° to 80° C. and under atmospheric pressure or slightly superatmospheric pressure of up to about 6 bar.

In process step (b), the intermediate reaction product from step (a) is decomposed, in the two-phase reaction mixture obtained from step (a), by means of a diazonium salt decomposition catalyst, preferably at from 20° to 80° C., especially from 40° to 60° C., nitrogen being evolved.

Examples of suitable decomposition catalysts are copper, tungsten and their compounds, preferably employed in amounts of from 0.01 to 0.1, especially from 0.02 to 0.03, mole per mole of methyl anthranilate, the catalyst being introduced in solid form or, if it is water-soluble, in the form of a concentrated aqueous solution. Particularly preferred catalysts are $CuCl_2$ and $Cu_2Cl_2$.

Surprisingly, surface-active quaternary ammonium salts, used in amounts of from about 0.01 to 0.1 mole per mole of methyl anthranilate, also prove to be suitable decomposition catalysts. Quaternary ammonium salts of the type $R-N^{\oplus}R'-_3 \cdot X^{\ominus}$ where R is a long-chain alkyl, R' is lower alkyl or hydroxyalkyl, eg. methyl or hydroxyethyl, and $X^{\ominus}$ is one equivalent of an anion, preferably chloride, have proved particularly suitable. Examples of such compounds are lauryltrimethylammonium chloride and stearyltrimethylammonium chloride.

The surface activity of the quaternary ammonium salts need not be particularly pronounced. Rather, it suffices if the salts are adequately organophilic, as is the case with, for example, tetrabutylammonium salts or trimethylbenzylammonium salts.

If copper salts are used as decomposition catalysts, surfactants quite generally accelerate the decomposition and accordingly increase the space-time yield. The amounts of these surfactants, which may be anionic, non-ionic or cationic, are preferably from 0.01 to 0.1 mole per mole of methyl anthranilate. In this case, again, the cationically surface-active quaternary ammonium salts prove suitable, since they also act as decomposition catalysts per se, a particular advantage being that the amount of copper salts required for a given effect is reduced to about one-tenth of that needed when using the copper salts alone.

Part of the sulfur dioxide is also evolved with the nitrogen liberated, and can be removed from the exit gas stream and recycled to process step (b) in a conventional manner, for example by washing with the solvent. The proportion of recoverable $SO_2$ can be increased by expelling the $SO_2$ from the reaction mixture by heating after completion of the reaction, ie. when no further nitrogen is evolved.

In an alternative embodiment, it is also possible to carry out the reaction with the $SO_2$ and the catalyst simultaneously. This method is as a rule to be preferred, since it permits an increase in the space-time yield and, because of the shorter total reaction time, the amount of by-products formed is lower.

The reaction product obtained from process step (b) is an aqueous organic mixture, of which the organic phase contains the methyl benzoate-o-sulfochloride.

In process step (c), this mixture is treated with an oxidizing agent at from 0° to 100° C., preferably from 20° to 50° C., under atmospheric pressure or slightly superatmospheric pressure, up to about 6 bar. This measure is based on the observation that methyl benzoate-o-sulfinic acid is formed as a by-product in step (b). Surprisingly, the sulfinic acid can readily be reoxidized to the sulfochloride, so that the yield of sulfochloride can be substantially increased. In principle, any oxidizing agent may be used, but for technical reasons hydrogen peroxide, and especially chlorine gas, are preferred. The requisite amount of oxidizing agent is from about 0.1 to 0.5 mole, as a rule from 0.2 to 0.3 mole, per mole of diazonium salt employed. The sulfinic acid can be detected by high pressure liquid chromatography. As a rule, the oxidation is complete after about 5–30 minutes.

Thereafter, the aqueous phase is separated from the organic phase. The aqueous phase is worked up in a conventional manner to recover the decomposition catalyst and is then discarded.

It is also possible to separate off the aqueous phase before the oxidative treatment, but as a rule it is advisable to effect the separation after the oxidation, because the aqueous phase takes up the water-soluble by-products, inter alia salts and residual sulfinic acid.

In process step (d), the organic phase obtained from (c), which contains the methyl benzoate-o-sulfochloride, is reacted with aqueous ammonia at from 0° to 50° C., preferably from 20° to 40° C. The amount of ammonia—which is preferably employed in a 10–25% strength by weight aqueous solution—is preferably from 3 to 4, especially from 3.2 to 3.5, moles per mole of the sulfochloride.

The saccharin formed in this reaction is taken up by the aqueous phase, and is precipitated therefrom in a conventional manner by acidifying with a strong acid, such as hydrochloric acid or sulfuric acid. The further purification of the saccharin can then be carried out in a conventional manner, for example by reprecipitation. The saccharin can also—again in a conventional manner—be converted to its sodium salt.

The organic phase remaining after formation of the saccharin can be recycled to the process, if necessary after intermediate purification by distillation.

The process according to the invention can be carried out batchwise or by conventional continuous techniques. Since, apart from the precipitation of the saccharin, the reactions involved are liquid phase reactions, continuous operation is technically particularly simple and also economical, compared to the saccharin syntheses of the prior art.

Based on methyl anthranilate employed, the crude saccharin (which is in fact more than 99% pure) is obtained in yields of 90% or more.

EXAMPLE 1

76 g (0.5 mole) of methyl anthranilate and 135 g of an aqueous sodium nitrite solution (containing 0.5 mole of $NaNO_2$) were added gradually in the course of 30 minutes to 196 g of 30% strength by weight aqueous hydrochloric acid (=1.61 mole of HCl) at from $-5°$ to $+10°$ C. The diazonium salt solution was then brought into contact with a solution of 200 ml of 1,2-dichloroethane and 42 g (0.65 mole) of $SO_2$ for 10 minutes at 20° C., with vigorous stirring.

5 g of an aqueous $CuCl_2$ solution (containing 0.9 g of Cu=0.014 mole) were added to the reaction mixture, which was then heated to 50° C., in the course of which a vigorous stream of $N_2$ was evolved. This process step required 80 minutes, after which the aqueous phase was separated off. 10 g (0.14 mole) of chlorine gas were then passed into the organic phase in the course of 10 minutes at 40° C., after which the mixture was stirred for 5 minutes.

250 g of aqueous ammonia (containing 33 g of $NH_3$=1.94 moles) were then added in the course of 5 minutes to the mixture obtained above, at 30°–40° C., with vigorous stirring. The phases were then separated. Finally, the saccharin was precipitated, in the form of a white crystal slurry, from the aqueous phase, at 30°–40° C., by means of 92 g of aqueous hydrochloric acid (containing 27 g of HCl=0.74 mole).

After conventional isolation and drying, the saccharin was obtained 99% pure (according to high pressure liquid chromatography); melting point 227°–229° C. The yield was 89.4%.

EXAMPLE 2

The method used was similar to Example 1, but methyl isopropyl ketone was used as the organic solvent, the $CuCl_2$ was added in solid form and only 5 g of $Cl_2$ were employed. The saccharin was obtained 99.6% pure and in a yield of 90.8%.

EXAMPLE 3

The method used was similar to Example 1, but diethyl ketone was used as the solvent and the $CuCl_2$ solution was added simultaneously with the $SO_2$ solution to the diazonium salt solution. The saccharin was obtained 99.8% pure and in a yield of 92.4%.

EXAMPLE 4

The method used was similar to Example 3, but in place of chlorine the equivalent amount (about 2.5 g) of hydrogen peroxide was used as the oxidizing agent. The saccharin was obtained 99.6% pure and in a yield of 93.1%.

EXAMPLE 5

The method used was similar to Example 1, but 20 g (about 0.08 mole) of lauryltrimethylammonium chloride were employed in place of the copper chloride; the decomposition of the diazonium salt required about 100 minutes. The saccharin was obtained 98.7% pure and in a yield of 72%.

EXAMPLE 6

The method used was similar to Example 5, but 0.5 g of the aqueous $CuCl_2$ solution (=about 0.001 mole of Cu) was employed in addition; the decomposition of the diazonium salt required only 40 minutes. The saccharin was obtained 99.8% pure and in a yield of 92.7%.

We claim:

1. A process for the preparation of saccharin by reacting an aqueous hydrochloric acid solution of o-methoxy-carbonylbenzenediazonium chloride with sulfur dioxide, which comprises:
   (a) reacting the aqueous diazonium salt solution with sulfur dioxide at from 1° to 100° C., in the presence of a water-immiscible or only partially water-miscible inert organic solvent forming a two-phase reaction medium,
   (b) decomposing the diazonium salt by treating the reaction mixture simultaneously or subsequently with a diazonium salt decomposition catalyst,
   (c) treating the aqueous organic reaction mixture, or the organic phase obtained after removing the aqueous phase, with an oxidizing agent selected from the group consisting of chlorine and hydrogen peroxide at from 1° to 100° C., and
   (d) reacting said organic phase with aqueous ammonia at from 0° to 50° C. and isolating the saccharin from the aqueous phase by acidifying with a strong acid.

2. A process as claimed in claim 1, wherein the organic solvent used is an aliphatic ketone of 4 to 10 carbon atoms.

3. A process as claimed in claim 1, wherein the organic solvent used is an aliphatic chlorohydrocarbon of 1 to 4 carbon atoms, containing up to two chlorine atoms per carbon atom.

4. A process as claimed in claim 1, wherein $CuCl_2$ or $Cu_2Cl_2$ is used as the diazonium salt decomposition catalyst.

5. A process as claimed in claim 4, wherein a surfactant is used conjointly with the copper salts to decompose the diazonium salt.

6. A process as claimed in claim 5, wherein a surface-active quaternary ammonium salt is used as the surfactant.

7. A process as claimed in claim 1, wherein a surface-active quaternary ammonium salt is used as the diazonium salt decomposition catalyst.

8. A process as claimed in claim 1, wherein chloride gas is used as the oxidizing agent.

9. A process as claimed in claim 1, wherein hydrogen peroxide is used as the oxidizing agent.

10. A process as claimed in claim 1, wherein the organic solvent used is selected from the group consisting of ketones and aliphatic chlorohydrocarbons which boil at from 50° to 150° C. under atmospheric pressure.

11. A process as claimed in claim 10, wherein the decomposition catalyst used to decompose the diazonium salt is at least one compound selected from the group consisting of $CuCl_2$, $Cu_2Cl_2$ and surface-active quaternary ammonium salts.

* * * * *